(12) United States Patent
Ahn et al.

(10) Patent No.: US 7,750,031 B2
(45) Date of Patent: *Jul. 6, 2010

(54) CAFFEIC ACID DERIVATIVE AND COMPOSITION CONTAINING THE SAME

(75) Inventors: Gi Woong Ahn, Suwon-si (KR); Byoung Kee Jo, Anyang-si (KR)

(73) Assignee: Thefaceshop Korea Co., Ltd., Gangnam-gu, Seoul (KR)

( * ) Notice: Subject to any disclaimer, the term of this patent is extended or adjusted under 35 U.S.C. 154(b) by 70 days.

This patent is subject to a terminal disclaimer.

(21) Appl. No.: 11/951,068

(22) Filed: Dec. 5, 2007

(65) Prior Publication Data

US 2008/0319059 A1    Dec. 25, 2008

(30) Foreign Application Priority Data

Jun. 19, 2007    (KR) ..................... 10-2007-0059740

(51) Int. Cl.
*A61K 31/41* (2006.01)
*C07D 249/08* (2006.01)

(52) U.S. Cl. .................... 514/383; 548/262.2

(58) Field of Classification Search ............... 548/262.2
See application file for complete search history.

(56) References Cited

U.S. PATENT DOCUMENTS

2008/0319060 A1*    12/2008    Choi et al. .................. 514/474

* cited by examiner

*Primary Examiner*—Susannah Chung
(74) *Attorney, Agent, or Firm*—Park Law Firm; John K. Park

(57) ABSTRACT

A caffeic acid derivative can be denoted by the chemical formula 1 below.

[Chemical formula 1]

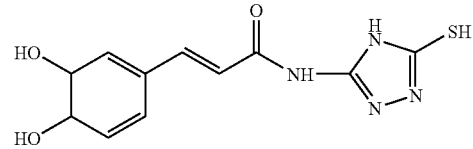

The present invention provides a caffeic acid derivative denoted by a chemical formula 1 as below and a composition containing the same. The preferable composition according to the present invention containing a caffeic acid derivative denoted as below contains a vitamins C further. And the composition can be the formulation for cosmetic material (cosmetics), medical material (medicine), foods (groceries), etc. The caffeic acid derivative according to the present invention as denoted by a chemical formula 1 is water-soluble and superior in antioxidant power so that it can stabilize the vitamins C effectively. The composition containing the caffeic acid derivative according to the present can increase whitening effect and further can prevent the skin from aging through effective activity of the vitamin C.

3 Claims, No Drawings

CAFFEIC ACID DERIVATIVE AND COMPOSITION CONTAINING THE SAME

CROSS-REFERENCE TO RELATED PATENT APPLICATIONS

This application claims the benefit of Korean Patent Application No. 10-2007-0059740, filed on Jun. 19, 2007, in the Korean Intellectual Property Office, the disclosure of which is incorporated herein in its entirety by reference.

BACKGROUND OF THE INVENTION

1. Field of the Invention

The present invention relates to a caffeic acid derivative and a composition containing the same, more particularly, relates to a new caffeic acid derivative capable of stabilizing a vitamin C, which is unstable in the water, effectively and having antioxidant power and a composition containing the same.

2. Description of the Related Art

Generally, because a vitamin C has powerful effect in restraining or improving of aging phenomenon for example wrinkle, decrease of elasticity, drying, hyperpigmentation, etc through variable physiological functions in a living body, it has long been applied to groceries, medicine, cosmetics, etc.

Especially, because a vitamin C deoxidizes a oxidized melanin to restrain unnecessary biosynthesis of the melanin by acting itself as a contestant which attempts to combine with the tyrosine competitively against the tyrosinaze which is a kind of the ferment of the rate-governed process of the melanin biosynthesis process, and by acting itself as a restrainer which restrains revelation of tyrosinaze, it shows general activity over a physiological process related skin whitening. (Postaire E. et al., Biochem. Mol. Int., 42:1023-1033 (1997))

Further, the vitamin C relates to a biosynthesis of collagen which is most relative to skin wrinkle. Proline and rycin, which are substituted by the hydroxyl group, are necessary in the biosynthesis of the collagen of the skin. And derivation of the hydroxyl group of the two amino acids is the vitamin C in the cell. That is, synthesis of the collagen can be processed smoothly when the hydroxyl group of vitamin C is transferred to the two amino acids. Thus, existence of the vitamin C is necessary to the biosynthesis of collagen. (Padh H., Nutrition Reviews, 49:65-70 (1991)

Actually, the content of vitamin C in the skin decreases as growing older. It is known that wrinkle increases due to the elasticity decrease of the collagen and decrease of synthesis of a new collagen. Accordingly, it is reported that maintenance of the content of the vitamin C is one of most effective ways to delay the process of the skin aging. (Kevin J. Lenton et al., Am. J. Clin. Nutrl, 71:1194-1200 (2000))

Although the vitamin C has variable effects as described above, it is very unstable against heat, light, oxygen, water, etc. Accordingly, there are serious problems in the stability of the vitamin C because its titer decreases and its color/smell changes when it is exposed in the air or when it is oxidized in the water solution especially. Various vitamin C derivatives to solve this instability have been studied and used but there is a problem that those derivatives are inferior in effectiveness to the pure vitamin C.

Accordingly, study for the formulation to stabilize the vitamin C has taken placed in various ways. For example, it has been tried to make chemical assembly with gluconic acid or urocanic acid or to impregnate into cyclodextrin, giolite, liposome, etc, physically. As another way, method to coat vitamin C also has been presented.

However, those ways described above does not show satisfactory stability in effectiveness and further some of them are not adaptable for the formulation of cosmetics. Further, a study to stabilize the vitamin C by applying various antioxidant agents including vitamin E has been tried but change of color/smell cannot be solved. (U.S. Pat. No. 4,938,969)

SUMMARY OF THE INVENTION

An object of the present invention is to provide a new caffeic acid derivative capable of stabilizing vitamin C effective and having powerful antioxidant power and a composition thereof.

A caffeic acid derivative according to the present invention has a chemical formula 1 as noted below.

[Chemical formula 1]

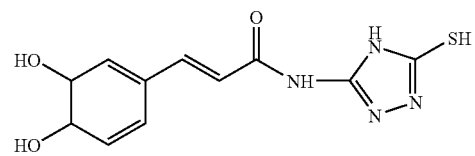

The caffeic acid derivative denoted by the chemical formula 1 can be used as an antioxidant agent or stabilization agent of the vitamin C.

Further a composition containing the caffeic acid derivative denoted by the chemical formula 1 according to the present invention also is presented.

It is preferable that the composition containing the caffeic acid derivative according to the present invention further contains a vitamin C.

It is preferable that the caffeic acid derivative is contained as much as 0.05~10 WT % (percently weight) with respect to the total weight of the composition and the vitamin C is contained as much as 0.1~20 WT % with respect to the total weight of the composition.

The composition according to the present invention can be selected from the group of compositions such as cosmetic material (cosmetics), medical material (medicine), foods (groceries), etc. It is preferable that the composition according to the present invention has the formulation of the cosmetic material having the caffeic derivative and the vitamin C together.

The caffeic derivative of the above chemical formula 1 is superior in solubility with respect to water and alcohol and can stabilize (protecting oxidation) vitamin C, which is unstable in the air or in the water, effectively. Accordingly, problems in the stability of the vitamin C, such that its titer decreases in the air and in the water or its color/smell changes, can be solved so that effectiveness of vitamin C can be improved. Further, because the caffeic acid derivative has powerful antioxidant power so that it can be applied to the skin well.

Additional aspects and/or advantages of the present invention will be set forth in part in the description which follows and, in part, will be obvious from the description, or may be learned by practice of the invention.

DETAILED DESCRIPTION OF THE INVENTION

Herein after the composition according to the present invention is described in detail.

Inventors of the present invention have long studied and tried to solve the instability problem of the vitamin C and have repeated studies with respect to various antioxidant agents in order to increase oxidation stability of the vitamin C in the formulation of the composition. The present invention can be completed by ascertaining that the noble caffeic acid derivative denoted by the above chemical formula 1 has powerful antioxidant power and stabilizes the vitamin C effectively. Especially, it can be studied that the caffeic acid derivative denoted by the chemical formula 1 is water-soluble and stabilizes the water-soluble vitamin C, which shows very unstable state in the water, more effectively. It is described in detail as below.

Vitamin C which the inventors of the present invention try to stabilize is a representative water-soluble pure vitamin. It is white powder type in dried powder state and it exists widely in natural world. Vitamin C is a common material which can be synthesized in the body of the plant and animal. However, unfortunately, fishes and primates including a human being cannot synthesize the vitamin C in his body. According, all lives including humans, who do not have mechanism to synthesize the vitamin C in the body, should supply necessary vitamin C through the ways such as ingestion of foods. Because vitamin C can maintain its stability when it is a dried power, there is no worry about change in quality within the period of circulation of goods when it is made in the forms of dried medicine capsule, pouch or an additive for a snack. Thus, there is not a problem in making product. There is no difficulty in making product as long as vitamin C is packed, but there is a problem that titer decreases and color/smell changes when vitamin C is exposed to the air or when vitamin C is in the water-solution sate.

Generally, cosmetic composition is based on liquid state formulation such as skin lotion, essence, cream, etc in most cases, various materials such as various additive, weighting material are contained, and the period of circulation of goods is relatively long within 1~3 years. In order to make vitamin C to cosmetic material, actual stabilization method to overcome the instability must be devised. Color of the vitamin C changed or destructed in quality varies to dark-brown over yellow and brown according to the degree of the destruction. This change in color happens to be recognized by customers as a change in color by the change in quality of all the materials in the cosmetic in the period of circulation. So the change in color can be a condition of dissatisfaction, refund, exchange so that it decreases marketability heavily.

A chemical formula of a caffeic acid is C9H8O4 and molecular weight of the caffeic acid is 180.16. The caffeic acid is contained generally in the phemolic chemical compound and it is a yellow crystal which is easy to be dissolved in the water or alcohol. It has two hydroxyls and it relates to a cinnamic acid. The caffeic acid and cinnamic acid are parts of carboxylic acid group, where a carbon is circulated, and it is a different chemical compound with caffeine. Although contained quality is different according to the kind of foods, the caffeic acid is contained in fruit including coffee bean, pear and medicinal plants/vegetables including basil, thyme, verbena, tarragon, oregano, turmeric, wood betony, rosemary, dandelion, etc. The caffeic acid acts as a depressant against the production of cancer and it is known as an antioxidant in the interior and exterior of the living body. It is known that the antioxidant power of the caffeic acid is superior to other antioxidant. Also, the caffeic acid can decrease the production of aflatoxin more than 95% and it can protect oxidation stress from being incurred.

According to the study of the inventors of the present invention, the caffeic acid has a powerful antioxidant power but it is not useful to stabilize water-soluble vitamin C because it can not be dissolved easily in the water. The phrase "To stabilize vitamin C" in the present invention means to protect the phenomenon where titer decreases and color/smell changes by the oxidation when the vitamin C is exposed in the air or when it is existed in the water solution. By the repeated studies of the inventors of the present invention for the derivative to dissolve the caffeic acid to the water, the inventors achieved a noble caffeic acid derivative denoted by the above chemical formula 1. The inventors can recognize that the caffeic acid derivative is highly water-soluble not only in the water but also in the alcohol. Also the inventors can recognize that the caffeic acid derivative can stabilize vitamin C easily and it has a powerful antioxidant power.

The caffeic acid derivative of the chemical formula 1 can be used as antioxidant or as oxidization stabilizing agent (oxidization protecting agent) of vitamin C and it can be named as [N-Mercapto-1,2,4-triazole) 3,4-Dihydroxy Cinnamide].

Also, the caffeic acid derivative of the chemical formula 1 can be synthesized from the caffeic ethyl ester denoted by the chemical formula 2 below and triazole derivative denoted by the chemical formula 3 below.

[Chemical formula 2]

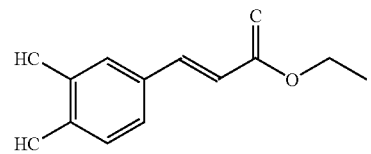

[Chemical formula 3]

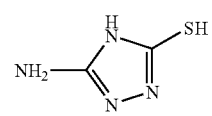

If a composition includes the caffeic derivative denoted by the chemical formula 1, it can be included to the composition according to the present invention.

According to the preferable embodiment, the composition according to the present invention contains the caffeic acid derivative and vitamin C together.

The composition according to the present invention can be a composition of cosmetic material (cosmetics), medical material (medicine), foods (groceries), etc. Especially, the composition according to the present invention can be composed by containing the caffeic acid derivative of the chemical formula 1 to the basic component which constitutes cosmetic material (cosmetics), medical material (medicine), foods (groceries), etc.

More preferably, the composition according to the present invention can be composed by containing the caffeic acid derivative and vitamin C to a basic component together.

It is preferable that the vitamin C is contained at 0.1~20 WT % with respect to the total weight of the composition. It is preferable that the caffeic acid derivative is contained at 0.05~10 WT % (percently weight) with respect to the total weight of the composition When the content of the vitamin C is less than 0.1 WT %, the effect due to the containing of vitamin C (skin whitening and wrinkle improvement effect according to the depression of melanin biosynthesis and oppression of collagen biosynthesis) is few. When the content of the vitamin C is more than 20 WT %, problems in stabilization of formulation can be happened.

When the content of the caffeic acid derivative is less than 0.05 WT %, it is difficult to achieve the effect of the present invention (stabilization of vitamin C, antioxidant power, etc). When the content of the caffeic acid derivative is more than 10 WT %, problems in stabilization of formulation can be happened.

The composition according to the present invention includes a formulation of cosmetic composition which contains the caffeic acid derivative and vitamin C together with contents described above, respectively. The cosmetic composition includes the caffeic acid derivative (and further vitamin C) beside common cosmetic basic component and it can include common container for example a stabilizing agent, a dissolvent agent, a colorant, a perfume, etc and a carrier. The composition according to the present invention can be made in the all the formulation which are made commonly in the cosmetic industry. Although it is not limited specially, toilet water, essence, lotion, paste, cleansing containing surfactant, cream, pack, gel, ointment, powder, patch, spray, etc can be included to the formulation.

When the formulation is one of paste, cream and gel, at least one selected from the group including animal oil, vegetable oil, wax, paraffin, cornstarch, tragacahth, cellulose derivative, polyethylene derivative, glycol, silicon, bentonite, silica, talc and zinc oxide can be used as a carrying agent component. For example, when the formulation of the cosmetic composition is toilet water or essence, a solvent, a solubilizing agent or an emulsifying agent can be used as a carrying agent and at least one selected from the group including water, ethanol, isopropanol, ethyl carbonate, ethyl acetate, benzyl alcohol, benzyl benzoate, propylene glycol, 1,3-butylene glycol, oil, glycerol aliphatic ester, polyethylene glycol and aliphatic ester of sorbitan can be used.

When the formulation of the cosmetic composition is power or spray, at least one selected from the group including lactose, talc, silica, aluminum hydroxide, calcium silicate and polyamide powder can be used as a carrying agent. Especially, when the formulation of the cosmetic composition is a spray, chlorofluorohydrocabon, prophane/butane or dimethylether can be used as a propellant, additively. When the formulation of the cosmetic composition is cleansing containing surfactant, at least one selected from the group including aliphatic alcoholsulfate, aliphatic estersulfate, sulphosuccinic acid monoester, isetionate, imidazolium derivative, methyltaurate, sarcosinate, aliphatic amide ether sulfate, alkylamid betain, aliphatic alcohol, fatty acid glyceride, fatty acid diethanolamide, vegetable oil, lanolin derivative and ethoxylated glycerol fatty acid ester can be used as a carrying agent.

The cosmetic materials composition according to the present invention is superior in antioxidant power because it contains the caffeic acid derivative and it acts effectively on the skin improving effect because it contains vitamin C and the vitamin C is stabilized. Accordingly, the cosmetic materials composition according to the present invention can improve the state of the skin so that it is useful in skin whitening, wrinkle improving and skin elasticity improving.

The embodiments of the present invention will be described in detail. The embodiments described below are provided to describe the present invention and thus the skilled person in the art can understand obviously that the technical scope of the present invention cannot be limited by the description of these embodiments.

Example of Production

The caffeic ethylester denoted by the chemical formula 2 10 g is dissolved in ethanol 50 ml, triazol derivate denoted by the chemical formula 3 5 g is applied, reflux stirring for 2 hours is performed and lastly it is cooled to the room temperature.

After strong hydrochloric acid 1 mL is applied, it is kept cool. By filtering the sediment and drying, the caffeic acid derivative 12 g (yield 80%) is achieved. By the result of the element analysis, it shows a proportions of "C, 48.92; H, 3.54; N, 19.98; O, 17.51; S, 11.45" so that it is identified that the achieved caffeic acid derivative is the material ($C_{11}H_{10}N_4O_3S_1$ (278.33): C, 47.47; H, 3.62; N, 20.13; O, 17.24; S, 11.52) which satisfies the chemical formula 1.

Example of Experiment 1

In order to identify solubility of the caffeic acid derivative achieved by the production example, 1 mg/mL, 10 mg/Ml and 100 mg/mL of the caffeic acid derivative are dissolved respectively while purified water and ethanol are used as solvent. A caffeic acid (Sigma, US), as a contrast agent, is dissolved with the same density and the same solvent and compared. The purified water and ethanol was placed at the water bath before the experiment to maintain their temperature at 25° C. The result of the experiment 1 is shown in table 1.

TABLE 1

(the result of solubility measurement)

| solvent | density (mg/mL) | solubility caffeic acid derivative | caffeic acid |
| --- | --- | --- | --- |
| purified water (25° C.) | 1 | dissolved completely | not dissolved |
|  | 10 | dissolved completely | not dissolved |
|  | 100 | dissolved completely | not dissolved |
| ethanol (25° C.) | 1 | dissolved completely | dissolved completely |
|  | 10 | dissolved completely | dissolved completely |
|  | 100 | dissolved completely | not dissolved |

As shown in table 1, it can be understood that the caffeic acid derivative according to the present invention can be dissolved by the purified water and the ethanol up to the density of 100 mg/mL. Also it can be understood that the caffeic acid of the contrast agent was not dissolved in the purified water and it could be dissolved in the ethanol up to 10 mg/mL.

Accordingly, it can be identified through the experiment 1 that the caffeic acid derivative according to the present invention is water-soluble and its solubility in the purified water and the ethanol is highly superior to the caffeic acid.

Example of Experiment 2

In order to identify antioxidant power of the caffeic acid derivative achieved by the production example, a free radical scavenging activity test was performed. The free radical scavenging activity test was a modified test of Kim et al. (Ko. J. Pharmacogn., 24(4), 299-303 (1993) and a reagent of DPPH (1,1-diphenyl-2-picryhydrazyl, Sigma company), as a stable free radical, was used.

150 μl of the caffeic acid derivatives with various density are prepared. Those prepared caffeic acid derivatives are applied to 0.2 mM DPPH solution (when blank, ethanol is used), respectively and placed at the room temperature for 30 minutes. Experimental groups to test absorbency at 517 nm are established. Cases to use purified water are established as contrast groups. After measurement of absorbency with respect to the experimental groups and the contrast groups, elimination activation effect of free radical is achieved by using the equation 1 below. The result of the measurement is shown in table 2.

$$\text{free radical elimination effect} = 100 - \frac{\begin{pmatrix}\text{absorbancy of the}\\\text{experimental group}\end{pmatrix} - \text{blank absorbancy}}{\text{absorbancy of the contrast group}} \times 100 \quad [\text{Equation 1}]$$

TABLE 2

(the result of antioxidant power measurement)

| caffeic acid derivative (ppm) | free radical elimination effect (%) |
|---|---|
| 3.125 | 22.0 |
| 6.25 | 39.1 |
| 12.5 | 64.8 |
| 25 | 87.9 |
| 50 | 95.1 |

It can be identified that the caffeic acid derivative has high free radical elimination capacity as shown in table 2.

Example of the Embodiment

Various cosmetic materials composition with components and proportions, as shown in table 3, are produced. In detail, the cosmetic materials composition includes vitamin 5 WT % (w/w) and the caffeic acid derivative 3 WT % (w/w) achieved by the above example of production beside common cosmetic materials composition.

Example of Comparison

Cosmetic materials composition with the same components and proportion without the caffeic acid derivative with respect to the cosmetic materials composition in the example of the embodiment was produced. Detailed component and proportion are shown in table 3.

TABLE 3

(component and proportion of cosmetic material composition)

| | component | example of embodiment content (wt %) | example of comparison content (wt %) |
|---|---|---|---|
| | vitamin C | 5.0 | 5.0 |
| | caffeic acid derivative | 3.0 | — |
| A | cetostearyl alcohol | 2.0 | 2.0 |
| | glyceryl stearate | 1.5 | 1.5 |
| | squalane | 5.0 | 5.0 |
| | liquid paraffin | 3.0 | 3.0 |
| | trioctanoin | 5.0 | 5.0 |
| | polysolbate | 1.2 | 1.2 |
| | sorbitan stearate | 0.5 | 0.5 |
| | tocopherol acetate | 0.2 | 0.2 |
| | cyclomethicone | 3.0 | 3.0 |
| | BHT (butylated hydroxytoluen) | 0.05 | 0.05 |
| B | glycerin | 4.0 | 4.0 |
| | 1,3-butylene glycol | 2.0 | 2.0 |
| | EDAT-2Na | 0.05 | 0.05 |
| | purified water | To 100 | To 100 |
| | perfume, antiseptics | moderate amount | moderate amount |

[Titer Measurement of Vitamin C]

In order to identify whether the caffeic acid derivative according to the present invention can maintain vitamin C, which is very unstable in the water, stably or not, titer maintaining capacity with respect to vitamin C was measured. Supposing that initial titer of the composition according to the example of embodiment and example of comparison was 100, titer after 1 month was measured at temperature 25° C. and 45° C., respectively. The result of the measurement was shown in table 4.

TABLE 4

(comparison of titer of vitamin C)

| remarks | example of embodiment | example of comparison |
|---|---|---|
| 25° C. | 99 | 70 |
| 45° C. | 85 | 40 |

It can be understood that the formulation (example of embodiment) where vitamin C was stabilized by the caffeic acid derivative is more stable that the formulation (example of comparison) as time goes, as shown in table 4)

Example of Experiment 4

In order to perform whitening clinical tests with respect to the cosmetic material composition, 20 healthy male/female adults who suffer speckle, freckle, hyperpigmentation, are divided into 2 groups at random. The example of embodiment where vitamin C is stabilized by the caffeic acid derivative is applied to the group A while the example of comparison is applied to the group B. The example of embodiment and comparison were applied 2 times per day during 12 weeks. To measure variance in the color of the skin, variance of blight of the skin (ΔL) was measured by a chromameter (Minolta CR300). Also objective observation with the naked eye by a plurality of experts and subjective observation with the naked eye by people in test are performed and the results were evaluated according to the rank. Evaluation was performed according to the 7 ranks as described below. The result of the evaluation is shown in table 5 below.

Reference for whitening effect evaluation; −3: heavily get worse −2: get worse −1: slightly worse 0: no variance 1: slightly improved 2: improved 3: highly improved.

TABLE 5

(the result of the measurement of whitening effect according to the clinical tests)

| the people in test | variance in the brightness of the skin | | objective evaluation by the experts | | subjective evaluation by the people in test | |
|---|---|---|---|---|---|---|
| | A | B | A | B | A | B |
| 1 | 7.0 | 4.9 | 3 | 1 | 3 | 2 |
| 2 | 6.9 | 5.1 | 3 | 2 | 2 | 3 |
| 3 | 7.7 | 4.8 | 3 | 3 | 3 | 3 |
| 4 | 7.3 | 4.1 | 2 | 2 | 2 | 1 |
| 5 | 8.0 | 4.9 | 3 | 2 | 3 | 1 |
| 6 | 7.5 | 5.4 | 3 | 2 | 2 | 1 |
| 7 | 8.8 | 5.2 | 3 | 1 | 3 | 0 |
| 8 | 6.7 | 4.8 | 2 | 3 | 3 | 2 |
| 9 | 7.4 | 5.9 | 3 | 2 | 3 | 3 |
| 10 | 8.7 | 5.6 | 2 | 1 | 3 | 3 |
| mean value | 7.62 | 5.07 | 2.9 | 1.9 | 2.7 | 2.0 |

It can be understood that the group A, where the product (example of embodiment) with the formulation where vitamin C was stabilized according to the present invention was applied, shows higher whitening effect in 3 test than the group B where the product (example of comparison), as shown in table 5.

Example of Experiment 5

Skin elasticity improving effect of the cosmetic material composition was measured as below. 20 healthy female above 20 years (mean age was 41 years) were divided 2 groups at the condition of temperature 22~25° C. and humidity 45. After the example of the embodiment and the example of the comparison were applied to the group A and B respectively 2 times per day (morning and evening) for 12 weeks, skin elasticity were measured by skin elasticity measuring device (Curometer MPA580, Conrage+Khazaka company, Germany) The results are shown in table 6. The results are denoted by the value of R8(R8(12 week)−R8(0 week)) of the curometer MPA50. Here, R8 value denotes the characteristic of the viscoelasticity.

TABLE 6

(the result of skin elasticity measurement)

| formulation in experiment | skin elasticity effect |
|---|---|
| example of embodiment | 0.69 |
| example of comparison | 0.34 |

It can be understood that skin elasticity of the example of the embodiment where vitamin C was stabilized by the caffiec acid derivative got increased about two times than that of example of the comparison.

Example of Experiment 6

Skin Patch Test

In order to identify the degree to incur skin stimulation, skin patch test were performed over the 20 female, each of them were in 20~30 and anyone of them have not suffered the overreaction over the skin stimulation in the past history and anyone of them does not suffer dermatopathy or skin allergy.

At first, test part were washed by 70% ethanol and dried. Prepared test material were loaded in 15 μl at the finn chamber (100×10, EPITEST, Finland). The patches chamber were patched at the interior portion of the forearms of the people in test and sealed tightly. The patches were removed in 24 hours and test portion was marked by a marking pen. Test parts were observed by the magnifying glass (3MC-150, DASOR, US) to observe whether erythema and edema was generated or not.

Skin reaction was evaluated by the evaluation reference and score according to the rule of the ICDRG (International Contact Dermatitis Research Group). Mean score is achieved by the equation 2 below. The result is shown in table 7.

(Evaluation reference and score of skin reaction)

| mark | score | evaluation reference |
|---|---|---|
| − | 0 | no reaction |
| ± | 0.5 | few or slight erythema |
| + | 1 | slight erythema, edema and papule with a distinct boundary |
| ++ | 2 | distinct erythema, edema and vesicle |
| +++ | 3 | heavy erythema, bulla and crust are generated |

$$\text{Mean score} = (\text{Score} \times \text{Number of response} \times 100 \times \tfrac{1}{2}) / (3 \, (\text{Maximum score}) \times \text{total number of people in test}) \quad \text{[Equation 2]}$$

TABLE 7

(the result of skin reaction evaluation)

| test material | 24 hour | | | 48 hour | | | mean score |
|---|---|---|---|---|---|---|---|
| | ± | + | ++ | ± | + | ++ | (n = 20) |
| example of embodiment | − | − | − | − | − | − | 0.00 |
| example of comparison | − | − | − | − | − | − | 0.00 |

It can be understood that the cosmetic material composition containing the caffeic acid derivative (example of embodiment) does not show skin stimulation and beside effect. Accordingly, it can be identified that the caffeic acid derivative according to the present invention is very safe so that it can be usefully adapted to the cosmetic material composition.

Based on the results of the example of experiments, some examples of formulations containing the caffeic acid derivative which stabilize vitamin C, which is very unstable in the water, according to the present invention are provides below. However, it should be noticed that this provision does not aim to limit the composition according to the present invention to formulations below.

Example of Formulation 1

Soft toilet water (skin lotion) was produced according to the component and content as shown in table 8.

TABLE 8

(component and content of the example of the formulation 1)

| component | content (ww&) |
|---|---|
| vitamin C | 1.0 |
| caffeic acid derivative | 1.0 |
| 1,3-butylene glycol | 6.0 |
| glycerin | 4.0 |
| oleyl alcohol | 0.1 |
| polysolbate 20 | 0.5 |
| ethanol | 15.0 |
| benzophenone-9 | 0.05 |
| perfume, antiseptics | few |
| purified water | to 100 |

Example of Formulation 2

Nutrition toilet water (milk lotion) was produced according to the component and content as shown in table 9.

TABLE 9

(component and content of the example of the formulation 2)

| component | content (ww %) |
|---|---|
| vitamin C | 3.0 |
| caffeic acid derivative | 3.0 |
| propylene glycol | 6.0 |
| glycerin | 4.0 |
| triethanolamine | 1.2 |
| tocopherol acetate | 3.0 |
| liquid paraffin | 5.0 |
| squalane | 3.0 |
| macadamianut oil | 2.0 |
| polysolbate 60 | 1.5 |
| soribitan sesquioleate | 1.0 |
| carboxyvinyl polymer | 1.0 |
| BHT | 0.01 |
| EDTA-2Na | 0.01 |
| perfume, antiseptics | few |
| purified water | to 100 |

Example of Formulation 3

Nutrition cream was produced in common method according to the component and content as shown in table 10.

TABLE 10

(component and content of the example of the formulation 3)

| component | content (ww %) |
|---|---|
| vitamin C | 5.0 |
| caffeic acid derivative | 3.0 |
| cetostearyl alcohol | 2.0 |
| glyceryl stearate | 1.5 |
| trioctanoin | 5.0 |
| polysolbate 60 | 1.2 |
| sorbitan stearate | 0.5 |
| squalane | 5.0 |
| liquid paraffin | 3.0 |
| cyclomethicone | 3.0 |
| BHT | 0.05 |
| delta-tocopherol | 0.2 |
| concentrate glycerin | 4.0 |
| 1,3-butylene glycol | 2.0 |
| santa gum | 0.1 |
| EDTA-2Na | 0.05 |

TABLE 10-continued (component and content of the example of the formulation 3)

| component | content (ww %) |
|---|---|
| perfume, antiseptics | few |
| purified water | to 100 |

Example of Formulation 4

Massage cream was produced in common method according to the component and content as shown in table 11.

TABLE 11

(component and content of the example of the formulation 4)

| component | content |
|---|---|
| vitamin C | 2.0 |
| caffeic acid derivative | 2.0 |
| propylene glycol | 6.0 |
| glycerin | 4.0 |
| triethanolamine | 0.5 |
| beeswax | 2.0 |
| tocopherol acetate | 0.1 |
| polysolbate 60 | 3.0 |
| soribitan sesquioleate | 2.5 |
| cetostearyl alcohol | 2.0 |
| liquid paraffin | 30.0 |
| carboxyvinyl polymer | 0.5 |
| perfume, antiseptics | few |
| purified water | to 100 |

Example of Formulation 5

Pack was produced in common method according to the component and content as shown in table 12.

TABLE 12

(component and content of the example of the formulation 5)

| component | content |
|---|---|
| vitamin C | 3.0 |
| caffeic acid derivative | 5.0 |
| propylene glycol | 2.0 |
| glycerin | 4.0 |
| carboxyvinyl polymer | 0.3 |
| ethanol | 7.0 |
| PEG-40 hydrogenated caster oil | 0.8 |
| triethanolamine | 0.3 |
| BHT | 0.01 |
| DDTA-2Na | 0.01 |
| perfume, antiseptics | few |
| purified water | to 100 |

As described above, the caffeic acid derivative according to the present invention is a new water-soluble oxidation stabilizing agent and it is a safe material without simulation to the skin, The caffeic acid derivative according to the present invention can make up the weak point of the caffeic acid that water-soluble vitamin C is hardly stabilized because it cannot be dissolved in the water. The caffeic acid derivative according to the present invention shows high antioxidant power. Thus the caffeic acid derivative according to the present invention can stabilize water-soluble vitamin C. Accordingly, the caffeic acid derivative according to the present invention can protect vitamin C in the product from being varied in color/smell so that it can activate application of the vitamin C to various products (cosmetic materials and medical materials).

Also, the composition according to the present invention can increase whitening effect and protect skin from aging because vitamin C is stabilized by the caffeic acid derivate and activity of the vitamin C in the skin can be performed effectively.

What is claimed is:

1. A caffeic acid derivative composition comprising vitamin C and a caffeic acid derivative as denoted by a chemical formula 1

[Chemical formula 1]

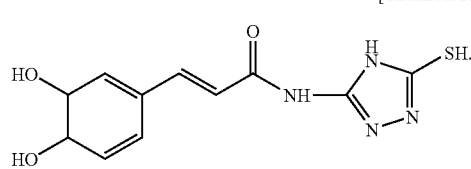

2. The caffeic acid derivative composition of claim 1, wherein the caffeic acid derivative composition further comprises:
a caffeic ethyl ester as denoted by the chemical formula 2, and
a trizole derivative as denoted by the chemical formula 3

[Chemical formula 2]

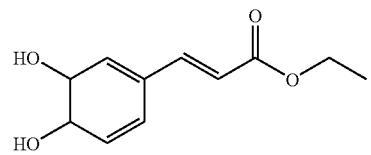

[Chemical formula 3]

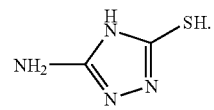

3. The composition of claim 1, wherein the caffeic acid derivative is of 0.05~10 WT % with respect to the total weight of the composition, and wherein the vitamin C is of 0.1~20 WT % with respect to the total weight of the composition.

* * * * *